United States Patent
Owen et al.

(10) Patent No.: US 9,017,613 B2
(45) Date of Patent: *Apr. 28, 2015

(54) ULTRAVIOLET PHOTOREACTOR FOR THE PURIFICATION OF FLUIDS

(71) Applicant: UVCleaning Systems, Inc., Beaverton, OR (US)

(72) Inventors: Mark D. Owen, Beaverton, OR (US); James Thorne, Portland, OR (US); Manoj K. Sammi, Beaverton, OR (US)

(73) Assignee: UVCleaning Systems, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/963,602

(22) Filed: Aug. 9, 2013

(65) Prior Publication Data

US 2013/0323128 A1 Dec. 5, 2013

Related U.S. Application Data

(63) Continuation of application No. 12/665,003, filed as application No. PCT/US2008/007654 on Jun. 20, 2008, now Pat. No. 8,506,886.

(60) Provisional application No. 60/936,642, filed on Jun. 20, 2007.

(51) Int. Cl.
*B01J 19/12* (2006.01)
*A61L 9/20* (2006.01)
(Continued)

(52) U.S. Cl.
CPC ............... *B01J 19/12* (2013.01); *A61L 9/205* (2013.01); *B01D 53/885* (2013.01);
(Continued)

(58) Field of Classification Search
USPC .................. 422/24, 105, 119, 186.3, 121; 250/432 R, 455.11, 492.3
See application file for complete search history.

(56) References Cited

U.S. PATENT DOCUMENTS 4,446,236 A 5/1984 Clyde
4,892,712 A 1/1990 Robertson et al.
(Continued)

FOREIGN PATENT DOCUMENTS

CN 201864596 6/2011
DE 20212730 1/2003
(Continued)

OTHER PUBLICATIONS

"About Solvatten;" Description of how the technology works, retrieved from the Internet on Jun. 18, 2012; http://www.solvatten.se/aboutaboutsolvatten/about-solvatten; 3 pages.
(Continued)

*Primary Examiner* — Sean E Conley
(74) *Attorney, Agent, or Firm* — Klarquist Sparkman, LLP (57) ABSTRACT

In order to disinfect and to detoxify a fluid, a photoreactor contains at least two light sources. One light source activates the catalytic function of a semiconductor material in the fluid to reduce the concentration of contaminants in the fluid, such as by breaking down organic contaminants into non-toxic compounds. A second light source acts directly on living biological entities to sterilize or kill them and thereby disinfect the fluid, and can also serve to activate a semiconductor photocatalyst that in turn causes further damage to biological contaminants. The semiconductor photocatalyst is desirably attached to an optically transmitting fiber substrate in the fluid. The second light source in one embodiment is external to the fluid and illuminates the photocatalyst through transmitting surfaces in a fluid containment vessel. The light sources can comprise respective sets of plural LEDs.

12 Claims, 5 Drawing Sheets

(51) Int. Cl.
  *B01D 53/88* (2006.01)
  *C02F 1/32* (2006.01)
  *C02F 1/72* (2006.01)
  *H05B 3/00* (2006.01)

(52) U.S. Cl.
  CPC .... *B01D 2255/802* (2013.01); *B01D 2259/804* (2013.01); *B01J 19/123* (2013.01); *C02F 1/325* (2013.01); *C02F 1/725* (2013.01); *C02F 2201/3222* (2013.01); *C02F 2201/3224* (2013.01); *C02F 2201/3227* (2013.01); *C02F 2201/326* (2013.01); *C02F 2209/20* (2013.01); *C02F 2209/24* (2013.01); *C02F 2305/10* (2013.01); *H05B 3/0052* (2013.01); *C02F 1/32* (2013.01)

(56) References Cited

U.S. PATENT DOCUMENTS

| | | |
|---|---|---|
| 4,966,759 A | 10/1990 | Robertson et al. |
| 5,032,241 A | 7/1991 | Robertson et al. |
| 5,118,422 A | 6/1992 | Cooper et al. |
| 5,449,236 A | 9/1995 | Hori et al. |
| 5,564,065 A | 10/1996 | Fleck et al. |
| 5,616,532 A | 4/1997 | Heller et al. |
| 5,658,530 A | 8/1997 | Dunn |
| 5,683,589 A | 11/1997 | Lasa et al. |
| 5,919,422 A | 7/1999 | Yamanaka et al. |
| 5,933,702 A | 8/1999 | Goswami |
| 6,129,893 A | 10/2000 | Bolton et al. |
| 6,221,259 B1 | 4/2001 | Kittrell |
| 6,238,630 B1 | 5/2001 | Iimura |
| 6,285,816 B1 | 9/2001 | Anderson et al. |
| 6,447,721 B1 | 9/2002 | Horton et al. |
| 6,524,447 B1 | 2/2003 | Carmignani et al. |
| 6,552,447 B1 | 4/2003 | Fuse |
| 6,562,309 B2 | 5/2003 | Burke et al. |
| 6,565,803 B1 | 5/2003 | Bolton et al. |
| 6,730,265 B2 | 5/2004 | Horton |
| 6,803,023 B1 | 10/2004 | Ohmori et al. |
| 6,872,241 B2 | 3/2005 | Soane et al. |
| 6,902,653 B2 | 6/2005 | Carmignani et al. |
| 7,473,481 B2 | 1/2009 | MacPhee |
| 7,534,356 B2 | 5/2009 | Saccomanno |
| 8,506,886 B2 | 8/2013 | Owen et al. |
| 8,834,805 B2 | 9/2014 | Owen et al. |
| 2002/0088945 A1 | 7/2002 | Matschke |
| 2002/0144955 A1 | 10/2002 | Barak |
| 2003/0150707 A1 | 8/2003 | Carmignani et al. |
| 2005/0000792 A1 | 1/2005 | Yamada et al. |
| 2009/0101420 A1 | 4/2009 | Guerra |
| 2009/0145855 A1 | 6/2009 | Day et al. |
| 2010/0178201 A1 | 7/2010 | Tribelsky |
| 2010/0209294 A1 | 8/2010 | Owen |
| 2010/0224562 A1 | 9/2010 | Rolchigo |
| 2012/0228236 A1 | 9/2012 | Hawkins |
| 2013/0118995 A1 | 5/2013 | Hawkins et al. |
| 2013/0180931 A1 | 7/2013 | Owen |

FOREIGN PATENT DOCUMENTS

| | | |
|---|---|---|
| DE | 102007049736 | 4/2009 |
| EP | 0838432 A1 | 4/1998 |
| EP | 0876907 A2 | 11/1998 |
| JP | 09/174046 A | 7/1997 |
| JP | 10-310779 A | 11/1998 |
| JP | H11 188269 | 7/1999 |
| JP | 3117334 U9 | 11/2005 |
| KR | 2004-0059420 | 7/2004 |
| WO | WO 2004/045756 A | 6/2004 |
| WO | WO 2008/156813 A1 | 12/2008 |
| WO | WO 2011/057015 A2 | 5/2011 |
| WO | WO 2012/012766 A2 | 1/2012 |
| WO | WO 2012/047670 A2 | 4/2012 |
| WO | WO 2013/176736 A1 | 11/2013 |

OTHER PUBLICATIONS

"Puralytics: Clean Air. Clean Water;" Description of the SolarBag, retrieved from the Internet on Jun. 26, 2009; http://www.puralytics.com/html/products.php; 1 page.

H. Tang, et al., "Electrical and Optical Properties of $TiO_2$ Anatase Thin Films," American Institute of Physics, Journal of Applied Physics, vol. 75(4); pp. 2042-2047, Feb. 15, 1994.

J.M. Herman, "Heterogeneous Photocatalysis: State of the Art and Present Applications," *Topics in Catalysis*, vol. 34, Nos. 1-4; pp. 49-65, May 2005.

Steven N. Frank and Allen J. Bard, "Heterogeneous Photocatalytic Oxidation of Cyanide Ion in Aqueous Solutions at $TiO_2$ Powder," Journal of the American Chemical Society, vol. 99:1; pp. 303-304, Feb. 5, 1977.

International Search Report, dated Oct. 21, 2008, issued in co-pending application No. PCT/US2008/007654.

Written Opinion of the International Searching Authority, dated Oct. 21, 2008, issued in co-pending application No. PCT/US2008/007654.

International Search Report and Written Opinion dated Jan. 7, 2010, issued in corresponding application PCT/US2008/007654, filed Jun. 20, 2008.

International Search Report and Written Opinion dated Jul. 27, 2011, issued by the International Searching Authority in corresponding application PCT/US2010/055510, filed Nov. 4, 2010.

International Search Report and Written Opinion dated Mar. 22, 2012, issued by the International Searching Authority in corresponding application PCT/US2011/045089, filed Jul. 22, 2011.

International Search Report dated Mar. 22, 2012, issued by the International Searching Authority in corresponding application PCT/US2011/045089, filed Jul. 22, 2011.

International Search Report and Written Opinion dated Apr. 27, 2012, issued by the International Searching Authority in corresponding application PCT/US2011/053504, filed Sep. 27, 2011.

Office action dated Aug. 29, 2013, issued in U.S. Appl. No. 13/931,667, filed Jun. 28, 2013.

Examiner's Report dated Sep. 12, 2013, issued by the Canadian Intellectual Property Office in Canadian National Stage Application No. 2,806,078, filed Jul. 22, 2011.

Examination Report dated Sep. 12, 2013, issued by the Canadian Intellectual Property Office in Canadian Patent Application No. 2,806,078, filed Jan. 18, 2013.

Examination Report dated Jul. 21, 2014, issued by the Canadian Intellectual Property Office in Canadian Patent Application No. 2,806,078, filed Jan. 18, 2013.

Examination Report dated Aug. 25, 2014, issued by the Australian Intellectual Property Office in Australian Patent Application No. 2011280900, filed Jul. 22, 2011.

ULTRAVIOLET PHOTOREACTOR FOR THE PURIFICATION OF FLUIDS

CROSS REFERENCE TO RELATED APPLICATION

This application is a continuation of U.S. National Stage application Ser. No. 12/665,003, entitled ULTRAVIOLET PHOTOREACTOR FOR THE PURIFICATION OF FLUIDS, filed on Dec. 16, 2009, which is the U.S. National Stage of International Application PCT/US2008/007654, entitled ULTRAVIOLET PHOTOREACTOR FOR THE PURIFICATION OF FLUIDS, filed on Jun. 20, 2008, which claims the benefit of U.S. Provisional Application Ser. No. 60/936,642, entitled ULTRAVIOLET PHOTOREACTOR FOR THE PURIFICATION OF FLUIDS and filed on Jun. 20, 2007, all of which applications are incorporated by reference herein.

TECHNICAL FIELD

The present technology is intended for use in the field of treating air, water, and other fluids to reduce contaminant concentrations, deactivate organisms, disinfect and otherwise purify the fluid.

BACKGROUND

Almost all of the air we breathe and liquids we drink are processed through fluid exchangers that heat/cool, process, and/or distribute as required. Such fluid exchangers include the HVAC system for building air, water delivery systems, or fluid dispensing equipment used in food processing. Processing the fluids may include any number of modifications to the fluid, but of most relevance here, the removal of unwanted contaminants by filtration methods, chemical treatment, or irradiation.

Types of contaminants that can be removed or rendered inactive in these processing steps can include:
1. Live biological matter, such as bacteria, viruses, protozoa, molds, etc. which might cause disease or stimulate allergies,
2. Dead biological matter, such as hair, dust, dander, excrements, and germs previously deactivated, etc. which might aggravate allergies or cause respiratory or digestive problems.
3. Organic compounds, such as from building materials, plant exhausts, drying paints, pesticides, industrial chemicals, human and animal wastes, etc.
4. Inorganic compounds such as metals, minerals, nitrates, phosphates, sulfates, etc. which are byproducts of industrial processing or fluid handling.
5. Pharmaceutical byproducts that remain in the fluid stream after municipal water treatment, and
6. Treatment byproducts from ozonation and chlorination, residuals of which may remain in the fluid stream after fluid (e.g., water) treatment.

No purification technology is effective at removing all of the undesired contaminants. For instance, air filtering in HVAC systems, even HEPA filtering, cannot remove all viruses and bacteria from a fluid stream and often accelerate their reproduction. As a result, most buildings in the world do not have adequate systems for treating indoor air quality. Similarly, filtration and chlorination methods are commonly combined for municipal water quality at the source, but these often do not address heavy metals, pharmaceutical byproducts, dissolved organic compounds, a growing list of germs, and such that is collected in the downstream water distribution system. Furthermore, any failures in maintenance of the chemicals and filters can worsen the water quality.

Additionally, existing technologies can create toxic waste streams in addition to the fluids they purify. Reverse osmosis, for instance, typically produces an output stream of more pure water and a second efflux stream that is more contaminated than the input fluid stream. Filtration technologies accumulate toxins and provide accelerated breeding grounds for germs, creating a toxic waste that must be treated, stored or it will become an environmental pollutant. Chlorination, ozonation, and other chemical methods can add chemicals into the fluid stream and result in byproducts of the chemical additives.

Ultraviolet light, especially deep UV light at wavelengths less than 300 nm, has been shown to be effective in disrupting the DNA of some germs and other organisms, rendering them unable to reproduce (sterilization), which can halt the spread of disease. Such deep UV light treatment deposits no chemicals in a fluid stream and in fact can also break down some contaminants in the fluid stream as well, either directly, indirectly through the generation of ozone or, if intensities are high enough, through photo-disassociation or photolysis. However, UV light treatment does not completely kill germs, nor remove organic waste or most other contaminants from the fluid stream unless very high intensities or very low wavelengths are used, which is often practically prohibitive. Typically used downstream of filtering technology, UV Germicidal Irradiation (UVGI) at 253.7 nm using low pressure mercury lamps is the fastest growing and best documented UV technique with accepted standards in place by many governing bodies. Low pressure Hg lamps are also efficient at generating almost all of their light at 253.7 nm, with wall-plug energy conversion efficiency up to >35%. Medium and high pressure mercury lamps and Xenon lamps can also be used to create higher intensities, although typically at the cost of reduced efficiency and lamp life.

An additional known UV technology, semiconductor photocatalysis, results when a suitable semiconductor material is irradiated by a light source with photon energies greater than its band gap (wavelengths less than the band gap wavelength) in the presence of moisture. These photons excite the semiconductor material to facilitate production of hydroxyl ions and other active species in the fluid at the semiconductor surface that break down certain organic materials through powerful oxidation and reduction reactions while leaving the semiconductor unchanged in the process. Nearly 1000 materials have been reported as successfully photocatalyzed in this way, mostly using anatase crystals of $TiO_2$, sometimes modified for increased photoreactivity.

However, there are many drawbacks that have restricted the use of semiconductor photocatalysis in purification applications, including relatively poor photon efficiency, long contact times, saturation of the surface with contaminants, and the practical issues of supplying a high surface area of photocatalyst into a fluid with uniform optical illumination at a suitable wavelength.

Therefore, a need exists for improvements in fluid purification technology.

BRIEF DESCRIPTION OF THE DRAWINGS

FIG. 4 is an exemplary embodiment of a fluid treatment apparatus comprising a plurality of chambers with light sources for delivery of plural wavelengths of light. FIG. 4 shows one half of an exemplary apparatus as FIG. 4 as a vertical sectional view through an exemplary apparatus.

FIG. 7 schematically illustrates an example of a photocatalytic reactor, which can take the form such as shown in FIG. 6A, in combination with a heat exchanger for transferring heat from fluid exiting from the reactor to fluid entering the reactor. FIG. 7 also illustrates exemplary parameter monitoring sensors that can be used in the apparatus together with an optional gas source that can be used to bubble air or oxygen into the reactor.

DESCRIPTION

The disclosure herein references a number of exemplary embodiments. The inventive features and method acts include all novel and non-obvious elements and method acts disclosed herein both alone and in novel and non-obvious subcombinations with other elements and method acts. In this disclosure, it is to be understood that the terms "a", "an" and "at least one" encompass one or more of the specified elements. That is, if two of a particular element are present, one of these elements is also present and thus "an" element is present.

What is needed is a fluid treatment technology that desirably has one or more of the following characteristics:

Detoxifies—Effective at reduction in concentration of at least certain monitored classes of organic and inorganic contaminants to regulated levels.

Disinfects—sterilizes (e.g., renders incapable of reproducing) or kills most living biological contaminants.

Local—purifies at the point of use.

Cost effective for a variety of real-world problems.

Simple—can be easily monitored and maintained.

Clean—reduces chemicals, heat, and fragile light sources in the fluid stream.

Efficient—uses photons and fluids efficiently and can couple excess heat outside the fluid stream.

A new type of photoreactor is described herein that, in one desirable form, exhibits all of these characteristics. In order to at least partially disinfect and to detoxify a fluid, the photoreactor contains at least two light sources. One light source activates the catalytic function of a semiconductor material in the fluid to reduce the concentration of contaminants in the fluid, such as by breaking down organic contaminants into non-toxic compounds, and removing heavy metals from the fluid. A second light source acts directly on living biological entities to sterilize or kill them and thereby disinfect the fluid, and can also serve to activate a semiconductor photocatalyst that in turn causes further damage to biological contaminants. The semiconductor photocatalyst is desirably attached to a fixed, optically transmitting fiber substrate in the fluid. The second light source in one embodiment is external to the fluid and illuminates the photocatalyst through transmitting surfaces in a fluid containment vessel. The fluid containment portion of the apparatus is desirably fabricated using materials that are highly resistant to damage by the fluid, the activated photocatalyst or the light.

Figure 1:
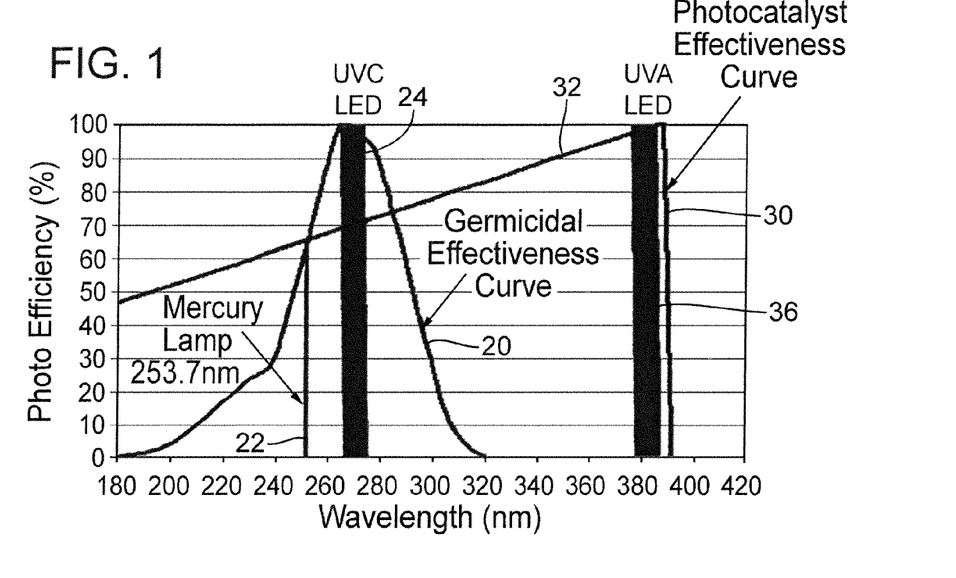
FIG. 1 is a graph of wavelength versus photoefficiency of a dual wavelength treatment apparatus utilizing one wavelength in the germicidal effectiveness band and another wavelength just below the band gap of an exemplary photocatalyst.

In one exemplary photoreactor, two or more wavelengths are chosen, at least one near the germicidal effectiveness curve peak, and one below the band gap of the photocatalyst. A desirable embodiment uses LED light sources with center wavelengths in the range of from 265-285 nm and 370-385 nm, such as shown in FIG. 1. Alternatively, Hg lamps operating with single emission lines at about 254 nm and/or 365 nm can be used together or in combination with LEDs. Other light sources can be used, as well as combinations thereof, such as combinations of Hg lamps and LEDs. More than two light sources can be used, such as to, for example, provide light at a wavelength of the band gap of a second catalyst, or to initiate photolysis.

The germicidal effect of light, optimally in the 250-300 nm range, is actually a photon effect, and the optimum germicidal efficiency has been shown to occur at wavelengths near ~265 nm—above the 253.7 nm generated by the low-pressure mercury lamps used in prior art. Additionally, as a photon effect, there are more photons at longer wavelengths for the same intensity level, so it is actually more efficient photo-chemically to use longer wavelength sources at or above the germicidal efficiency peak, but still in the germicidal band. It is also expected that a broadband light source will sever a broader range of bonds in DNA molecules than a narrowband source such as a laser, a low-pressure Hg lamp or other narrow spectral emission source, thereby reducing the likelihood of natural cellular repair mechanisms restoring viability to a UV-sterilized organism, known as "dark repair". Thus, a broadband source can overcome the dark repair phenomenon.

Although this can be varied, desirably light intensity for photocatalysts should be within a range of from 1 mW/cm2 to 50 mW/cm2, with a more desirable photocatalytic light intensity being from 3-15 mW/cm2. Light flux for germicidal treatment (from the first light source) is recommended to be sufficient to deliver a cumulative dose of at least 16 mJ/cm2, with treatment cumulative doses of 300 mJ/cm2 or more being required for 4-log reduction of some viruses. In accordance with this disclosure, the synergistic and complementary effects of the photocatalytic and germicidal process is believed to allow the same treatment results to be obtained at lower power intensities, lowering the germicidal cumulative dose requirement to at least 10 mJ/cm2.

Note that photocatalytic oxidation is also a photon activity, and again, that there are more photons for a given UV intensity for higher wavelengths, and that only wavelengths below the bandgap of a semiconductor catalyst have any useful effect. Additionally, higher wavelengths penetrate most fluids more deeply with less attenuation, furthering the efficient use of photons.

According to FIG. 1, a graph of wavelength versus photoefficiency is shown in this figure. Overlaid on this figure is a germicidal effectiveness curve 20 illustrating wavelengths of light that can be used to disinfect fluid, such as water or air. As one can see from this figure, the peak germicidal effectiveness is generally at wavelengths between 260 and 280 nanometers with 265 nanometers being an approximate peak germicidal effectiveness wavelength. In accordance with embodiments disclosed herein, a first light source emitting light having a wavelength within the germicidal effectiveness curve is provided. Such a light source can be a low pressure mercury lamp which has a very narrow spike of light at 253.7 nm within this germicidal effectiveness curve. As another alternative. LED light sources can comprise this first source of light. Exemplary LEDs are commercially available at a variety of wavelengths. For example, LEDs can be selected that are at a wavelength centered on 265 nm or at some other wavelength between 260 and 285 nm. Light emitting diodes are available that each have emission wavelengths over a band with full width half maximum (FWHM) of 10 nm or greater centered on a selected wavelength. By using relatively wide band LEDs of this type, effective light intensities can be delivered over a wider wavelength range than is the case for low pressure mercury lamps, thereby increasing the effectiveness of the germicidal activity of the first light sources. In particularly desirable embodiments, a multiplicity of LEDs are used such as several hundred LEDs light sources for each light source. The tight spike of light at 253.7 nm from a mercury lamp is indicated at 22 in FIG. 1. The wider band of light available from LED light sources is indicated at 24 in FIG. 1. In addition, semiconductor photocatalysts have a band gap with photocatalytic activity being promoted by light at wavelengths below the band gap. FIG. 1 illustrates an exemplary photocatalytic effectiveness curve 30 for a semiconductor catalyst, in this case for $TiO_2$, a majority of which is in the anatase crystalline form, with a band gap of 388 nm. As one can see from the slope of the curve 32 in FIG. 1, the closer to the band gap wavelength of the photocatalyst, the more effective light is at photoactivating the catalyst. Desirably, for this particular catalyst, light below 388 nm is desirable and light between 340 nm and 388 nm provides a desirable effect. It should be noted that photocatalytic activity is also achieved to some extent by light from the first light source which is also below the band gap of the photocatalyst. In FIG. 1, a second light source comprising plural LEDs having a wavelength band indicated at 36 centered at a wavelength below 388 nm is shown.

Figure 2:
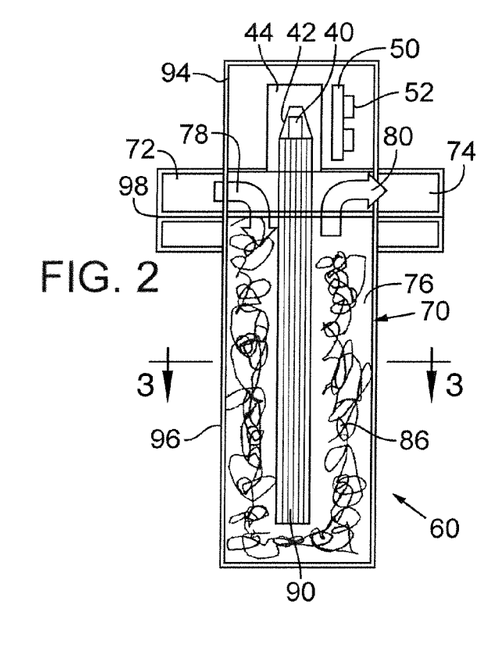
FIG. 2 schematically illustrates an exemplary embodiment of a plural wavelength fluid treatment apparatus.

In FIG. 2, the first and second light sources are shown schematically mounted at 40 to a circuit (not shown) within a protective reflector 42 positioned within a heat sink 44. The heat sink, for example, can be of metal such as an aluminum extrusion and can have fins or other heat radiating features. Extrusion 44 can be coated, for example with a highly reflective material to achieve high optical reflectivity and protection. The LEDs of the light sources can be driven by control circuitry 50 supplied with alternating current or DC current voltage at a power input 52. Input 52 can include a transformer and rectifier circuitry for converting AC power to DC power and to electrically isolate the control circuitry. The control circuitry can be operable to turn power to the LED light sources on and off to turn the LEDs on and off, for example if the temperature within the photoreactor becomes too high. Also, the control circuitry can continuously operate the LEDs, except when off, or can provide a pulsed power source to the LEDs so that the light is pulsed. By including a plurality of LEDs for each of the lights, typically several hundred LEDs (with one prototype example utilizing over 1900 LEDs for the second light source), these LEDs can be pulsed together by the control circuit, sequentially pulsed, or sequentially pulsed in groups so as to optimize electrical efficiency, thermal efficiency and/or electrical-to-photocatalytic conversion efficiency.

Another embodiment is schematically shown in FIG. 2. Note that the dual wavelength emitter, in this case, for example, the first light source, comprises plural LED at or near a 265-285 nm wavelength band and the second light source comprises plural LEDs operating at or near a 365-385 nm wavelength band. LEDs emitting in the 265-285 nm germicidal band are commercially available from Sensor Electronic Technology, Inc. and other vendors. LEDs emitting in the 365-385 nm band are available from Nichia Corp. and other vendors.

The apparatus of FIG. 2 comprises an exemplary photoreactor 60 comprising a housing 70. The housing 70 comprises a fluid inlet 72 and a fluid outlet 74. A fluid flow path is defined by the housing from the inlet 72 to the outlet 74. The illustrated housing comprises an internal chamber 76 through which fluid flows. Arrow 78 indicates incoming fluid whereas arrow 80 indicates outgoing fluid. The fluid can be gas, liquid (e.g., water), slurries (e.g., waste treatment slurries or food containing slurries), as non-limiting examples. A substrate 86 is contained within the housing. Substrate 86 comprises, and is desirably entirely of, a material that transmits light at the frequencies of the light sources being used for fluid treatment. Substrate 86 can be fibers or other photocatalytic material supporting substrates. As specific examples, the fibers can be in the form of mesh, mats or agglomerations. The substrate or support matrix supports a photocatalytic oxidant material with semiconductor catalysts being specific examples. A specific exemplary material is Quartzel® (explained below) that has $TiO_2$ on glass fibers. Desirably the photocatalyst has a much greater surface area than the supporting matrix. As a specific example, it is desirable that the photocatalyst has a surface area that is more than 10 times the surface area of the substrate, with a surface area in excess of 100 times the surface area of the matrix being more preferred. The photocatalyst is preferably adhered to the substrate rather than being presented as a particulate slurry through which fluid passes. The embodiment of FIG. 2 also comprises an elongated waveguide 90 extending into the interior 76 of the housing 70. The waveguide is optically coupled to the light sources 40 in this example, so that light travels along the wave guide for dispersion into fluid to be treated. The wave guide can be provided with surface irregularities to assist in dispersing the light into the fluid.

The housing 70 can comprise plural housing sections or portions, such as an upper housing section 94 and a lower housing section 96 that are joined together, such is at a joint 98. Desirably the lower housing section containing the photocatalytic material is detachable mounted to the upper housing portion 94. The upper housing portion can be mounted, such as by brackets not shown, to a fixed supporting structure. The detachable lower housing section 96 can be removed for replacement and/or refurbishing of the photocatalyst material. Thus, the reactor of FIG. 2 can comprise a cartridge type reactor.

Figure 3:
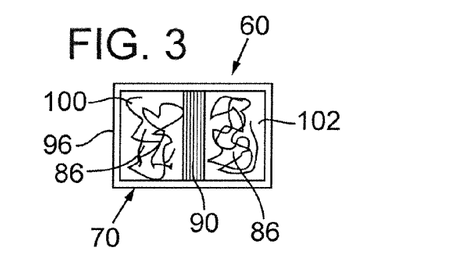
FIG. 3 is a vertical sectional view through the apparatus of FIG. 2, taken along lines 3-3 of FIG. 2.

In the embodiment of FIG. 2, fluid flows downwardly along one side of the wave guide 90, flows across the bottom edge of the wave guide, and then upwardly along the opposite side of the wave guide. Thus, in this example, the wave guide forms a portion of a baffle structure for directing fluid flow through the housing. In addition, the interior wall of housing section 96 can be coated or otherwise provided with an optically reflective material to assist in retaining light within the housing. Also, the interior wall of housing 96 can be coated with or otherwise contained for support photocatalytic material to further assist in the photocatalytic degradation of contaminants in the fluid being treated. As can be seen in FIG. 3, with this specific construction, the fluid flow path has a first entering flow path section 100 and a second exiting flow path section 102, and the fluid flow path cross sections and lengths may be readily increased or decreased without changing the overall module design.

It should be noted that the flow rate through the apparatus can, for example, be reduced to zero to provide in effect a batch treatment of fluid with the fluid being treated and then removed from the chamber following treatment. In a less desirable embodiment, the same passage can be used for both the inlet and outlet, for example in a batch treatment approach.

Again the light can be coupled into the optical wave guide 90, such as into the edge of a sheet like optical waveguide. Optical coupling can be enhanced by using an optical coupler, such as by using a gel or optical fluid or an optical taper, such as those used for UV LED encapsulant or optical coupling of UV optics. The optical waveguide performs as an optical coupling media, coupling light from the light source effectively into the fluid. The optical waveguide can be of other configurations. However, in the FIG. 2 form, the optical wave guide is positioned along at least a portion of a fluid passageway between an inlet and an outlet thereof. The waveguide can be sheet-like with edges. In one exemplary form, the waveguide comprises at least a portion of a baffle with fluid passing along both sides of the waveguide as the fluid travels past the baffle. The optical waveguide can have the edges reflectively coated on the sides other than those used for coupling and would perform as a light guide from the emitters to the fluid. The surface of the optical coupling media can be modified to increase side emission through major surfaces thereof by scattering the light traveling down the optical waveguide sideways out of the media and into the fluid. For example, a textured surface can be used to enhance side emission. The surface can also be coated to minimize coupling losses. By varying the modifications to the surfaces of the media, it is possible to achieve uniform side emission intensity over reasonable lengths.

As mentioned above, the housing can comprise plural parts, in this example the upper housing section 94 and the lower housing section 96. Section 94 can be a fixed element containing connections to fluid inlet and outlet plumbing and to an electrical supply. This fixed element can also contain control electronics and light sources as appropriate. The second section 96 desirably contains fluid conduits with photocatalyst inside. These housing sections can be connected together in any suitable manner, such as using a threaded fitting or a bayonet-type connection. Electrical power and signal connections between the two parts can be made, for example, through annular contacts on each part. Fluid sealing between the two parts can be effected through use of gaskets, o-rings or other sealing mechanisms.

As another aspect of embodiments, the support matrix can, for example, be light-transmitting at both (or more if more than two bands of light are used for fluid treatment) wavelengths bands of light (bulk material internal transmission >50% through 1 centimeter thickness) mesh and/or fibrous filter, with glass wool as one specific example. The PCO (photocatalyst oxidant) can, for example, be a coating or adhered particles, such as nanoparticles. Photocatalytic semiconductor materials comprise, for example a number of metal oxides and chalcogenides known to be effective oxidants under UV illumination, including, but not limited to, $TiO_2$, $WO_3$, $SrTiO_3$, $BaTiO_3$, $ZnO$, $ZnS$, $ZnSe$ and $SnO_2$. For practical application, the specific surface area of the photocatalyst should be at least 10 times the area of the substrate, and a higher surface area contributes to faster photochemistry rates under illumination. A preferred embodiment is a coating of $TiO_2$ on a loosely woven silica fiber substrate, prepared so that a majority (more than 50%) of the $TiO_2$ is in its anatase form and so that the specific surface area of the coating is approximately 1000 times the surface area of the fiber substrate, and the coating thickness is less than one micron. Quartzel® is a commercially-available example of such a substrate with $TiO_2$ adhered thereto and is available from Saint-Gobain.

Figure 4:
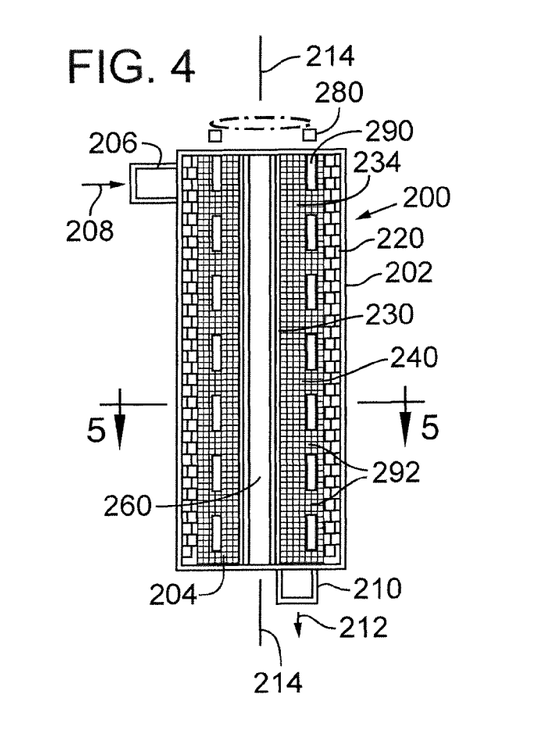
Figure 5:
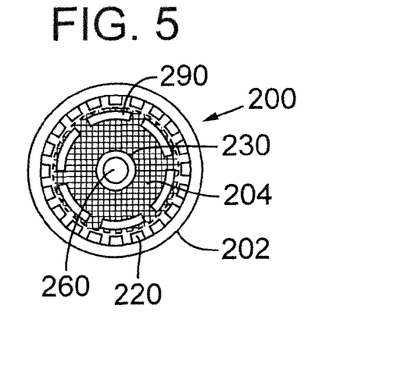
FIG. 5 is a horizontal sectional view, taken along lines 5-5 of FIG. 4, as if the entire apparatus were present in FIG. 4.

Another embodiment of an exemplary photoreactor 200 is shown in FIGS. 4 and 5. This embodiment 200 comprises a housing 202 having an interior 204. An inlet 206 receives fluid (indicated by arrow 208) for delivery into the interior of the housing. An outlet 210 from the housing delivers fluid, indicated by arrow 212, from the housing following treatment. Although other shapes can be used, in the embodiment of FIGS. 4 and 5, the housing 202, although other shapes can be used, is of right cylindrical shape having a longitudinal axis indicated by line 214. The illustrated reactor 200 comprises a filter 220, such as a carbon filter, for providing initial filtration of the fluid as it flows into the reactor 200. The reactor 200 in this example also has an interior cylindrical wall 230 extending the length of the reactor with an annular chamber being 234 existing between the exterior wall 202 and interior wall 230 through which the fluid flows. A substrate 240, such as previously described, supports one or more semiconductor photocatalyst materials adhered thereto. The substrate is indicated by cross hatching in FIG. 4 and FIG. 5 for convenience.

A first light source 260, which can comprise a low pressure mercury lamp, can be disposed in the interior of wall 230. Lamp 260 is illustrated as an elongated lamp and is operable to deliver UVC light to fluid flowing through the reactor. Wall 30 is light transmissive to this UV light. Alternatively, the mercury lamp 260 can be replaced by another light source such as plural LED light sources, for example disposed within chamber 230 or about a support positioned within inner chamber 230. A second light source can comprise, for example, a plurality of LED light sources represented schematically at 280 in FIG. 5. These LEDs can, for example, be arranged in a circular configuration and can be optically coupled to a light transmissive cylinder 290 positioned within the chamber. Wave guide 290 comprises a right cylindrical wave guide of a light transmissive material with apertures therethrough to permit the flow of fluid radially inwardly towards the center of the housing during treatment.

In the FIG. 4 embodiment, the photoreactor 200 can thus, for example, comprise a housing 202, which, in some configurations can be reflective or have a reflective interior wall surface. Inside the housing, for example, in progressively decreasing cylinders, the following components can be positioned: a filter medium 220, a photocatalyst containing, supporting or coated support 240, such as a silica fiber wool, mesh and/or matrix, an optical waveguide 200 with flow holes or apertures, some being numbered at 292, and a second photocatalyst treatment cylinder (interiorly of cylinder 290), a central housing component such as cylinder 230, which can, for example, be a quartz or FEP tube, and at the center a low pressure mercury lamp 260. UV LED light sources can be mounted near one or both ends of the waveguide and edge coupled into the waveguide. The wave guide can also be surface modified to provide enhanced surface emission. As a result, both the photocatalyst mesh or support inside and outside the waveguide would be exposed to UV light. Additionally the innermost surface of the photocatalyst would also be irradiated by the center mounted germicidal light. Fluid in this embodiment passes in from the outer ring, flow through both UV exposure zones, and out the outlet port 210, shown in FIG. 4 at the bottom of the housing.

The photoreactor housing components that contain the fluid and photocatalyst should not contaminate the fluid, should not impede or be damaged by the flux of light activating the photocatalyst, and should not be damaged by the photocatalytic processes. UV-transparent glasses generally meet these requirements. A desirable embodiment would use transparent or light transmissive plastic materials that are mold-able and are not susceptible to photocatalytic oxidant attack. Fluorinated ethylene propylene (FEP) is an exemplary desirable material that meets these requirements.

The filter media 220 shown on the outer ring of the photoreactor of this example can be optional depending on the particular configuration and fluid purification requirements. The filter can include, for example, active carbon or heavy metal removal materials, such as in a porous flow-through cylinder.

Another embodiment involves replacing the center mercury lamp 260 as shown in FIG. 4 with a second optical waveguide, with UV LED light sources or laser light sources of wavelengths near the peak of the germicidal effectiveness curve coupled (e.g., end coupled) to the wave guide.

Figure 6:
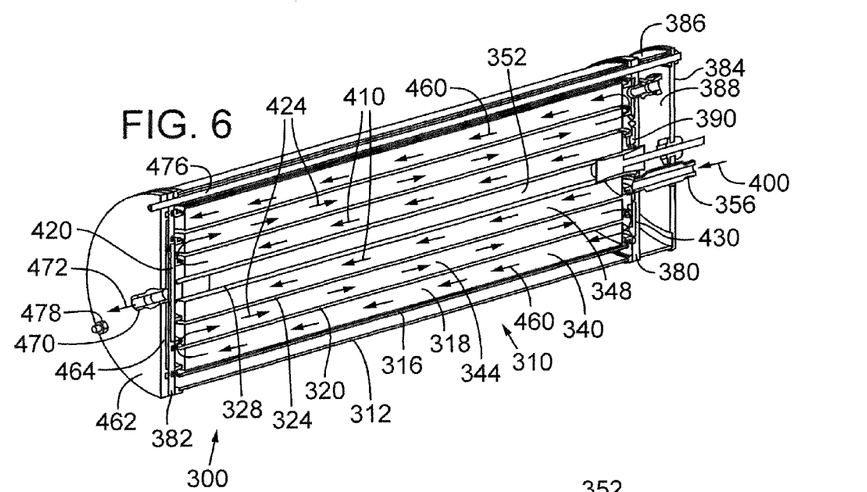
FIG. 6 is a broken away isometric view of another form of plural wavelength photoreactor showing a plurality of chambers included therein, with FIG. 6 being broken away to show one half of the exemplary reactor.
Figure 6A:
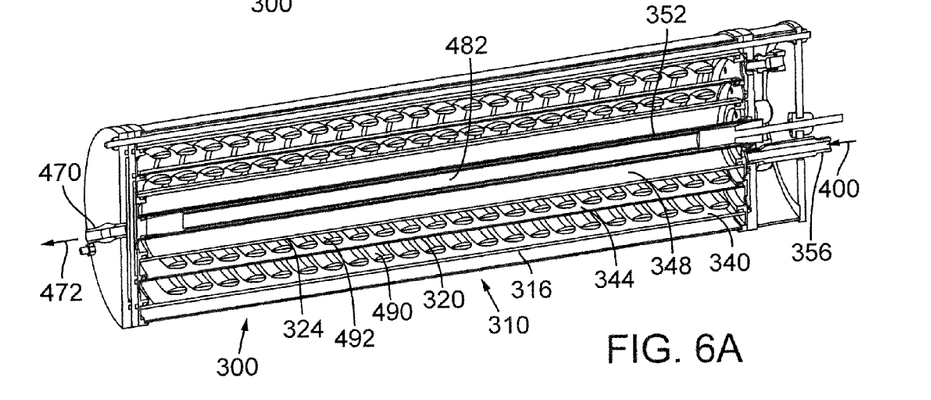
FIG. 6A is similar to FIG. 6 except that FIG. 6A illustrates plural LED light sources positioned within chambers of the apparatus of FIG. 6A and with a low pressure mercury lamp in a central chamber of FIG. 6A. The LED light sources in FIG. 6A are shown contained in flexible materials wound around a wall of one of the housing components of the apparatus.

FIGS. 6 and 6A illustrate yet another embodiment of a photoreactor 300 in accordance with this disclosure. With reference to FIG. 6, in this embodiment a housing 310 comprises an outer protective shell portion 312, which can be of right cylindrical construction. The housing also comprises a first interior wall portion 316, which can also be of a right cylindrical construction concentric with wall 312. The interior surface 318 of wall portion 316 can be coated, for example, with an optically reflective material. An interior wall 320, inside wall 316 and which can also be of right cylindrical construction and concentric with wall 316, has a diameter which is less than the diameter of wall 316. Wall 320 in this embodiment is comprised of, and desirably is entirely of, a material that is light transmissive to light being used in treatment of fluid passing through the housing. A wall 324 is positioned interiorly of wall 320 and also can comprise a right cylindrical wall concentric with the walls 320 and 316. Wall 324 can be comprised of the same material as wall 320. Yet another wall 328 is provided in this example interiorly of wall 324. Wall 328 can also be of right cylindrical construction and can be concentric with wall 324, wall 328 is of a lesser diameter than wall 324. The walls 316 and 320 thus define a first annular chamber 340 therebetween. In addition, the walls 320 and 324 define a second annular chamber 344 therebetween. Also, the walls 324 and 328 define a third annular chamber 348 therebetween. The interior wall 328 in this example defines a lamp receiving chamber 352 for receiving a first light source, such as an elongated low pressure mercury lamp or a plurality of LED light sources comprising the first light source. A first end wall 380 closes one end of the cylindrical housing section. A second end wall 382 closes the opposite end of the housing. An outer end wall 384 adjacent to end wall 380 together with a wall portion 386, in this case a cylindrical wall portion, together define an end chamber 388 within which electrical and other components of the photoreactor can be placed.

An inlet 356 passes through wall 384 and wall 380 and communicates with a first manifold passageway 390 (which can, for example, be circular in cross-section). Fluid 400 entering inlet 356 passes through manifold 390 into the interior most chamber 348 and flows therethrough in the direction indicated by arrows, some of which are numbered as 410 in this figure. End wall 382 is provided with a manifold 420 in an interior surface that communicates with chamber 348. In this example, fluid passes from chamber 348, reverses direction in manifold 420 and flows in the direction of arrows, some of which are indicated at 424 in FIG. 6, through chamber 344 toward end wall 380. As this fluid approaches end wall 380, the fluid enters another manifold 430 formed in the interior surface of wall 380. The manifold 430 is sealed from manifold 390. As an example, the manifold 430 can be annular in shape. Fluid is directed through manifold 430 and reverses direction so as to flow from chamber 344, through manifold 430, and into the chamber 340. The fluid thus flows through chamber 340 in a direction opposite to the direction of flow through chamber 344, as indicated by arrows, some of which are numbered as 460 in FIG. 6. An outer end cap or end wall 462 is mounted to wall 382 and has a manifold 464 defined in the surface thereof adjacent to wall 382. Fluid flows from chamber 340 into manifold 464 and exits through an outlet 470 as indicated by an arrow 472. O-ring gaskets or other seals can be used to seal the various manifolds from one another and to isolate the respective annular flow chambers from one another except through the manifolds as described above.

The housing components can be secured together in any suitable manner. As a specific example, a plurality of through bolts, one being numbered at 476 in FIG. 6, can be inserted through the end walls and through the space between walls 312 and 316 with nuts or other fasteners being used to secure the respective ends of the bolts to clamp the housing components together. For example, a nut 478 is shown secured to an unnumbered through bolt in FIG. 6. In this specific example, three through bolts are used to secure the components together.

Figure 9:
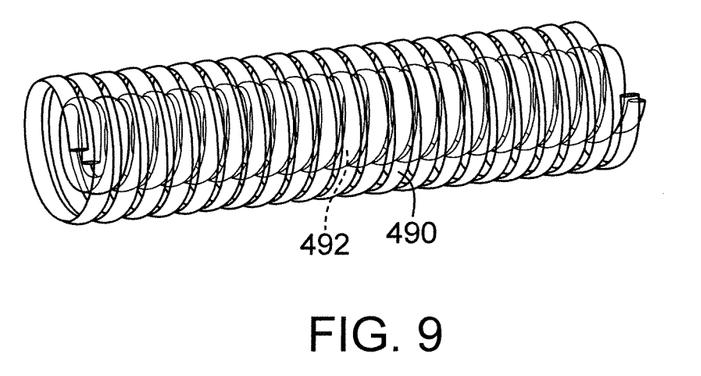
FIG. 9 illustrates an exemplary light source comprising two strings of plural LED light sources contained in flexible light transmissive tubing that is wound around cylindrical walls (not shown in FIG. 9) of a housing of an exemplary photoreactor, such as the FIG. 6A photoreactor.

With reference to FIG. 6A, a low pressure mercury vapor lamp 482 is shown within the innermost chamber 352. The second light source comprises a plurality of LEDs are shown in the respective chambers 340 and 352. These LEDs can be provided as a plurality of LED light sources inner connected in tubing to isolate the LEDs from the fluid to be treated. Sections of this tubing are numbered at 490 and 492 in FIG. 6A. One continuous tube can be used, for example, in each chamber. Desirably the tubes are of a flexible material. The tubes are of a light transmissive material. The tubes can be spirally disposed around respective interior walls of the photoreactor. Thus, a first spirally disposed tube 490 containing multiple LED light sources can be wound about wall 320 or otherwise mounted in the space between walls 316 and 320. In addition, a second set of LED light sources in tubing 492 can be provided disposed spirally around the wall 324 or otherwise disposed between walls 320 and 324. Spirally disposed tubing containing LEDs is simply one exemplary approach for positioning the LEDs within the fluid being treated. Although not shown in FIG. 6 or 6A, photocatalyst containing or supporting substrate is positioned in the chambers 340, 344, and 352 such as previously explained. FIG. 9 illustrates tubing 490,492 containing LED light sources in a spiral configuration around walls, not shown in this figure.

Thus, in an example represented by FIGS. 6 and 6A, a centrally mounted germicidal lamp, such as a mercury lamp, or alternatively an optical wave guide coupled to a light source such as the plurality of LED light sources, or plural LEDs positioned to deliver light without the use of a wave guide, at a first light source frequency is provided. A photocatalyst supporting substrate is disposed in a chamber about the centrally mounted light source such as concentrically therewith. Surrounding housing sections, such as concentric tubes of a light transmissive material with quartz, glass or FEP being specific examples, are also provided. LED light sources, such as comprising a second light source, are disposed relative to these additional chambers to excite photocatalysts on photocatalyst supporting substrates within such chambers to result in the reduction in the concentration of contaminants in the fluid being treated. The light is dispersed throughout the chambers by scattering effects of the substrate which may, for example, comprise a mesh or wool of silica or glass fibers as previously explained. These LED light sources can be contained in spiral round strips or tubes to separate the LED light sources from the fluid being treated. This provides protection to the light sources. This can also provide a cooling effect. The LED light sources can be retained in a shrinkable FEP tube. The fluid in the example of FIGS. 6 and 6A travels down the center and through each concentric layer in a serpentine flow, exiting from the outer cylinder.

In the FIGS. 6 and 6A embodiment, germicidal light is provided centrally where the fluid flow is fastest, and photocatalytic activity is excited by spiral windings of LEDs at each concentric tube. The fluid velocity decreases with each level, increasing the contact time within the reactor to enhance the photo degradation process.

Additionally, the preparation and attachment of the photocatalyst to the optically transmissive substrate desirably is done in a manner that enhances the active surface area. In these embodiments, the photocatalytic specific surface area is desirably 10-1000 times the surface area of the supporting substrate, increasing adsorption, adsorptive capacity, and photon utilization, while also reducing the degradation time for a particular contaminant significantly in comparison to a slurry of photocatalyst.

Another embodiment desirably comprises a heat exchanger operable to thermally couple the input and output streams without actually mixing them together. Generally, cooler water is preferred for drinking, so the output of the photocatalytic reactor in a drinking water example is desirably as cool as possible. However, photochemical processes generally proceed more rapidly at higher temperatures. Because the light sources and electrical circuits in a photocatalytic reactor produce heat, the output fluid is generally warmer than the input. Thermally coupling the input and output streams assists in cooling the output while reciprocally warming the input.

Figure 7:
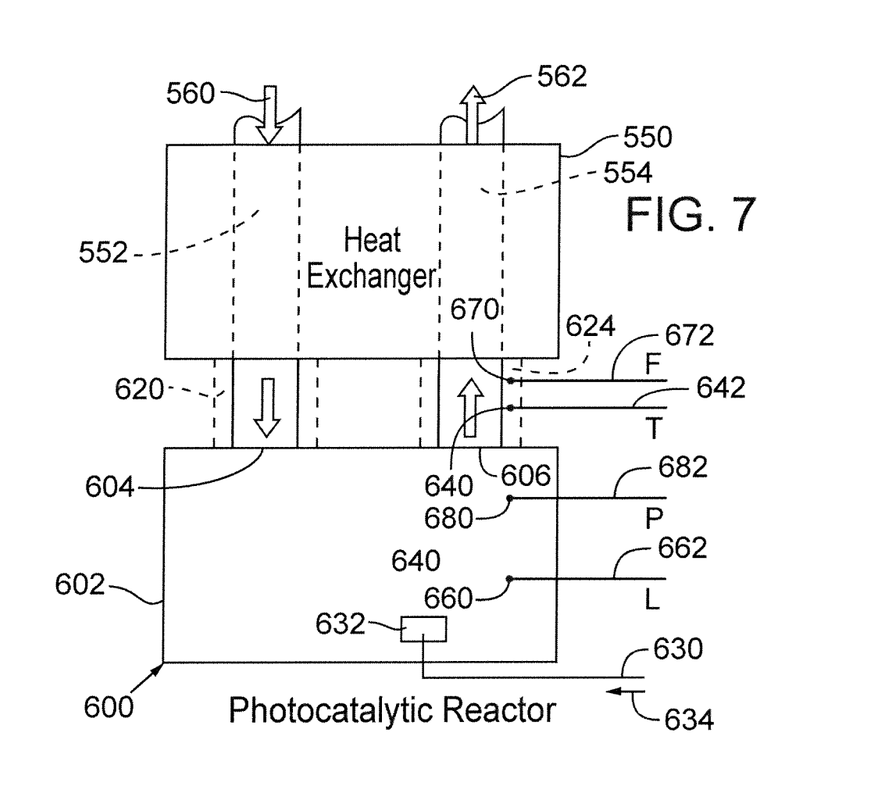

As shown in FIG. 7, the heat exchanger 550 comprises a thermally-conductive body through which both input and output fluid streams flow. The thermally-conductive body can be comprised of metal, such as aluminum or another good thermal conductor, and the conduits 552, 554 for the two streams can be spaced closely within the block to improve thermal conductivity. In addition, the input and output conduits 552, 554 can contain internal structures to promote turbulent flow, branch through small capillaries, or otherwise improve thermal coupling between the fluid and the exchanger.

In the embodiment of FIG. 5, fluid is indicated to enter conduit 552 of the heat exchanger 550 by arrow 560. Fluid is indicated to exit from the heat exchanger by arrow 562. A photocatalytic reactor 600 having a housing 602 is shown in FIG. 7. Reactor 600 comprises an inlet 604 and an outlet 606. The interior of reactor 600 can be the same as previously discussed with first and second light sources and a photocatalyst supporting substrate within the reactor to provide disinfectant and photocatalytic treatment of fluid passing through the reactor.

An optional filter indicated by dashed lines 620 is positioned upstream of light sources within the photocatalytic reactor, such as upstream of inlet 604 (although the filter 620 can be within the photocatalytic reactor). An additional filter 624, shown in dashed lines, is illustrated downstream of the light sources and at the outlet 606 of the photcatalytic reactor. Filter 624 can be included inside the reactor as well. One or both of these filters 620, 624 can be provided depending upon the particular treatment application. For example, filter 620 can be utilized to remove bulk contaminants. Filter 624 can be used to remove residual degraded components following the photocatalytic treatment.

During photocatalytic treatment, it is possible for the oxygen level within the photocatalytic reactor to drop to the point where the photocatalytic processes are slowed below desirable levels. The oxygen level can be sensed within the photoreactor, for example, by one or more oxygen sensors coupled to a controller responsive thereto. The controller can operate a valve to deliver air, or another oxygen source along a line 630 to, for example, an oxygen or air dispersion mechanism 32, such as a bubbler, within the photoreactor. Air or oxygen is shown entering line 630 by arrow 634. A controller can control a valve and/or a pump to pump air into the bubbler or otherwise open an air or oxygen source such as a pressurized source.

Various sensors can be used in connection with the photocatalytic reactor of FIG. 7. For example, a temperature sensor indicated at 640 can be provided downstream of the lights, such as in an outlet conduit, or within the photocatalytic reactor itself A signal on line 642 corresponding to the sensed temperature can be delivered to a controller (see for example controller 700 in FIG. 8). In response to the temperature exceeding a threshold, the controller can operate the photocatalytic reactor to, for example, protect the components of the reactor from excessive heat. For example, the controller 700 can control power to the light sources to shut off the light sources selectively so that the light sources are not adding heat to the system. Alternatively, the controller 700 can control power to the light sources to operate them in a way to more effectively generate light and reduce heat generation. For example, the controller 700 can cause the light sources to be pulsed, operated sequentially, or to have groups of LED light sources operate sequentially.

One or more light sensors can be provided, one of which is indicated at 660 in FIG. 7 to provide an output on a line 662 corresponding to the level of the sensed light. In response to the sensed light, the controller can control, for example, the current delivered to the light sources to adjust the intensity of the light sources or otherwise control the operation of the light sources to adjust the level of light being delivered within the reactor. One or more flow sensors can also be included in the system. For example, one flow sensor as indicated at 670 in FIG. 7. The flow sensor 670 provides a signal on line 672 corresponding to the detected flow rate. The controller 700, in response to the detected flow rate, can control the operation of the photocatalytic reactor. For example, if the flow rate drops to zero and batch treatment of fluid is not being performed, the controller can cause the light sources to shut off to eliminate a build up of heat under these low flow situations. It should be noted that the flow rate at the flow passage can be zero if desired.

In addition, one or more performance sensors, one of which is indicated at 680 in FIG. 7, can be provided for delivering an output signal on a line 682 indicating a performance characteristic of the system. For example, the performance sensor can be a $CO_2$ sensor or a total organic carbon sensor for monitoring organic contaminate concentration.

Alternatively, the performance sensor can be a sensor for a particular inorganic contaminant such as lead. The performance sensors can be positioned at the output of the reactor, or at both the input and output of the reactor, as well as elsewhere within the reactor for monitoring purposes. Again, a plurality of different types of performance monitoring sensors can be used. These sensors can also be used in the control of the reactor. For example, light intensities can be increased to increase photocatalytic treatment of the fluid if increased treatment levels are indicated to be desirable for degrading contaminants in the specific fluid being treated to desired levels.

Figure 8:
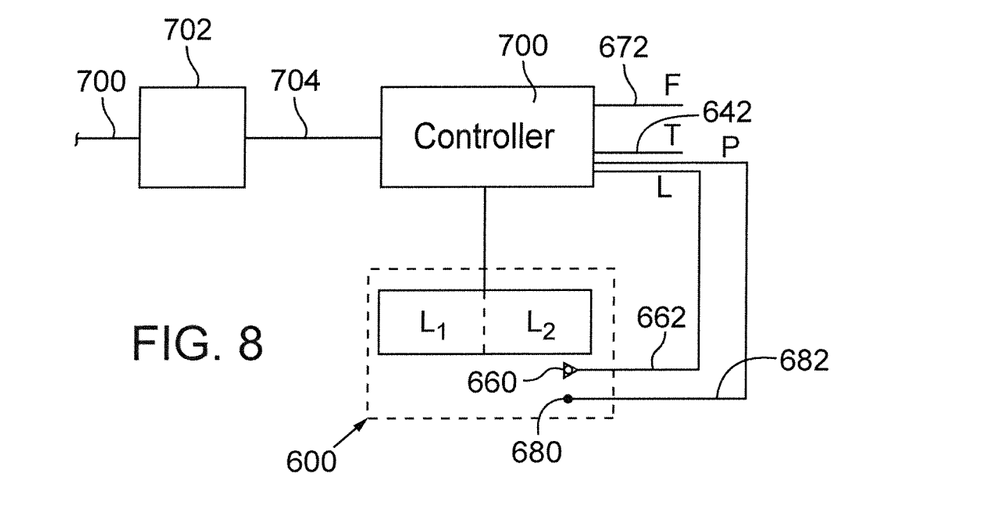
FIG. 8 illustrates an exemplary controller that can be used to control light sources; for example a first light source $L_1$ and a second light source $L_2$, which can be a plurality of LED light sources, the controller being responsive to control parameters.

It should be noted that the controller 700 desirably is a digital controller with suitable drivers, although an analog controller or analog/digital controller can be used. Input power to the controller is provided along a line 700. Power conversion circuitry, such as AC to DC or DC to DC conversion circuitry can be provided, as indicated at 702, with the desired power being delivered along the line 704 to the controller. In FIG. 8, the first and second light sources, such as plural LED light sources, or other combinations of light sources are indicated at $L_1$ and $L_2$. In this example, $L_1$ refers to the light source used for disinfectant purposes and $L_2$ refers to the light source used for photocatalytic treatment, it being recognized that light source $L_1$ can also contribute to the photocatalytic treatment. Also, although these light sources $L_1$ and $L_2$ are shown in separate boxes in FIG. 8, the $L_1$ and $L_2$ light sources can be comingled. For example, one or more light sources $L_1$ may be interspersed with one or more light sources $L_2$ within the photoreactor.

In yet another embodiment, air may be bubbled through or otherwise introduced into the fluid flow within or upstream from the photocatalytic reactor. Insufficient oxygen present in the water can result in a slowing of photocatalytic processes.

In yet another embodiment where air is the fluid, an air filter in a HVAC system can be replaced with or coupled with a photocatalytic filter, illuminated from one side with a germicidal light and one side with LED light sources to activate the photocatalyst, or with LED light sources of both wavelength bands illuminating one or both sides.

Specifically, the system can use one or more of the following technologies alone and in combinations and sub-combinations with one another. A desirable embodiment combines all of these technologies. In a portable unit, upstream or downstream filtration can be eliminated or be of a reduced weight.
- A. Upstream or downstream standard or activated filtration for bulk contaminants to avoid soiling the photoreactor, or to catch any residuals after the photoreactor
- B. Deep UV light optimally matched to the germicidal effectiveness curve with broadband emission for maximum photon efficiency.
- C. A second wavelength light source for efficiently generating photons nearer to the bandgap of the photocatalyst up to the maximum sustainable level on all surfaces with a photocatalyst.
- D. A photocatalyst layer prepared with large specific surface area and well attached to a semi-rigid, transparent mesh within a reflective reactor housing to efficiently use all photons at both wavelengths.
- E. An optical subsystem that couples light into the fluid stream in a uniform way with minimal losses and without having light sources in direct contact with the fluid stream.
- F. Solid state light sources for optimum coupling of light, minimal heating of the irradiated surfaces, and efficient coupling and control. The ability to have on/off, intensity and pulse width control further extends the light source's capabilities.
- G. Performance sensor(s), such as a CO2 sensor or a Total Organic Carbon sensor for monitoring organic contaminant concentrations, or a sensor for a particular inorganic contaminant such as Pb, at the output of the reactor, or at both the input and output of the reactor, to allow performance monitoring of the system.

Further examples of embodiments of a fluid treatment apparatus in accordance with this disclosure are disclosed by the following groupings of elements.
- A. An apparatus for treating fluid comprising:
    a housing comprising an inlet for receiving fluid to be treated and an outlet for delivering treated fluid, the housing defining a fluid flow path between the inlet and the outlet;
    a light transmitting substrate in the fluid flow path;
    a semiconductor photocatalyst adhered to the substrate, the photocatalyst comprising at least a first photocatalyst with a first band gap wavelength;
    at least one first light source operable to deliver light to fluid in the housing to be treated, said at least one first light source emitting at least one first band of light having a center wavelength in the range from 250 nanometers to 285 nanometers so as to provide disinfection treatment of the fluid; and
    at least one second light source operable to deliver light to the photocatalyst in the fluid in the housing to be treated, said at least one second light source emitting at least one second band of light having a center wavelength at or below the first band gap wavelength so as to provide a photocatalytic reduction of contaminant concentrations in the fluid.
- B. An apparatus according to A wherein the at least one first light source comprises a low pressure mercury lamp operable to deliver light to fluid in the housing to be treated, the light comprising a first band of light having a center wavelength of 253.7 nanometers.
- C. An apparatus according to A wherein the at least one first light source comprises a plurality of first LED light sources.
- D. An apparatus according to A wherein the at least one second light source comprises a plurality of second LED light sources.
- E. An apparatus according to A wherein said at least one first light source comprises a first set comprising a plurality of LED light sources operable to emit light at a wavelength in a first band centered at a first wavelength and having a full width half maximum band that is at least ten nanometers wide.
- F. An apparatus according to A wherein all of the light sources included in the at least one first light source are operable to deliver energy to the fluid in the housing at a level of no less than 10 millijoules per square centimeter.
- G. An apparatus according to A wherein the photocatalyst comprises TiO2, the majority of which is of an anatase crystalline form and wherein the at least one second light source comprises a plurality of LED light sources operable to emit at least one band of light centered at a wavelength in the range of from 345 nanometers to 388 nanometers.
- H. An apparatus according to A wherein the photocatalyst comprises at least first and second semiconductor photocatalysts.

I. An apparatus according to A wherein the surface area of the photocatalyst is more than 10 times the surface area of the substrate.

J. An apparatus according to A wherein the intensity of light from the second light source is in the range of from one to fifty milliwatts per square centimeter.

K. An apparatus according to A comprising a heat exchanger coupled to the inlet and outlet for transferring heat from fluid exiting the outlet to fluid entering the inlet.

L. An apparatus according to A wherein the substrate comprises quartz, silica or glass fibers.

M. An apparatus according to A wherein the housing comprises a plurality of chambers, each chamber containing light transmitting substrate with photocatalyst adhered to the substrate, the housing defining a fluid flow path from the inlet through the chambers to the outlet.

N. An apparatus according to M comprising at least three concentric annular chambers comprising right cylindrical chamber walls, the exterior most chamber wall comprising a light reflective material, the other cylindrical walls comprising light transmissive material, an interior lamp receiving chamber being provided within the interior of the innermost annular chamber for receiving at least one first light source, said at least one first light source comprising a low pressure mercury lamp, the at least one second light source comprising a plurality of LED light sources mounted to the walls of the annular chambers.

O. An apparatus according to N wherein the LED light sources are positioned in light transmitting tubes mounted within at least one chamber.

P. An apparatus according to O wherein the tubes comprise flexible material which is spirally disposed within at least one of the chambers.

Q. An apparatus according to P wherein the tubes are of a light transmitting fluorinated ethylene propylene (FEP).

R. An apparatus according to O wherein the light transmissive material is selected from the group consisting of glass, silica, quartz and fluorinated ethylene propylene.

S. An apparatus according to A comprising at least one elongated optical wave guide extending into the interior of the housing from a first location, at least one of the first and second light sources being optically coupled to the at least one elongated wave guide with the wave guide guiding light from the said at least one optically coupled light source into fluid in the housing.

T. An apparatus according to S wherein said at least one optical wave guide comprises fluorinated ethylene propylene.

U. An apparatus according to S wherein said at least one wave guide comprises a wall surface and wall surface modifications that diffuse light passing along the wave guide outwardly from the wave guide through the wall surface.

V. An apparatus according to U wherein said surface modifications comprise one or more of a surface coating, chemical etchings, mold-texturing, photo-ablation, and sand blasted regions.

W. An apparatus according to A comprising control circuitry operable to selectively turn on and off the first and second light sources.

X. An apparatus according to A comprising control circuitry operable to vary the intensity of light from the first and second light sources.

Y. An apparatus according to A comprising at least one temperature sensor for monitoring the temperature of fluids treated by the light sources and a controller responsive to the temperature sensor and operable to interrupt light from the first and second light sources in the event the temperature exceeds a temperature threshold.

Z. An apparatus according to A comprising at least one flow sensor for monitoring the flow of fluid through the housing and a controller responsive to the flow sensor and operable to interrupt the delivery of light to fluid in the housing in the event the flow of fluid drops below a flow threshold.

AA. An apparatus according to A comprising at least one performance sensor for testing one or more properties of the fluid flowing through the housing and for providing an output corresponding to said one or more properties.

BB. An apparatus according to AA wherein the at least one performance sensor comprises at least one carbon dioxide sensor that monitors carbon dioxide levels within the housing to monitor photo degradation of organic materials.

CC. An apparatus according to A comprising at least one fluid filter positioned one or both of a location upstream in the fluid flow path from the first and second light sources or a location downstream in the fluid flow path from the first and second light sources.

DD. An apparatus according to A comprising a housing having a plurality of housing components, a first housing component comprising a mount for coupling the first housing component to a fixed support surface, a second housing component being detachably mounted to the first housing component and defining at least one chamber within which the substrate and adhered photocatalyst are positioned, the first housing component comprising the fluid inlet and the fluid outlet and a power receiving input.

EE. An apparatus according to A comprising an air source coupled to the housing and operable to selectively add air to fluid within the housing.

In addition, fluid treatment methods corresponding to treatment steps accomplished by the embodiments set forth in the disclosure and the claims below, form a part of this invention.

The above examples, as well as examples of embodiments set forth elsewhere in this disclosure further serve to illustrate the invention. Having illustrated and described the invention with reference to exemplary embodiments, it will be apparent to those of ordinary skill in the art that these embodiments can be modified in arrangement and detail without departing from the inventive principles set forth herein. We claim all such embodiments that fall within the scope of the following claims.

We claim:

1. An apparatus for treating fluid comprising:
    a housing comprising an inlet for receiving fluid to be treated and an outlet for delivering treated fluid, the housing defining a fluid flow path between the inlet and the outlet;
    a light transmitting fiber substrate in the fluid flow path;
    a semiconductor photocatalyst adhered to the substrate, the photocatalyst comprising at least a first photocatalyst with a first band gap wavelength;
    at least one first light source operable to deliver light to fluid in the housing to be treated, said at least one first light source emitting at least one first band of light having a center wavelength in the range from 250 nanometers to 285 nanometers so as to provide disinfection treatment of the fluid; and at least one second light source operable to deliver light to the photocatalyst in the fluid in the housing to be treated, said at least one second light source emitting at least one second band of light having a center wavelength at or below the first band gap wavelength so as to provide a photocatalytic reduction of contaminant concentrations in the fluid.

2. An apparatus according to claim 1 wherein said at least one first light source comprises a first set comprising a plurality of LED light sources operable to emit light at a wavelength in a first band centered at a first wavelength and having a full width half maximum band that is at least ten nanometers wide.

3. An apparatus according to claim 1 wherein all of the light sources included in the at least one first light source are operable to deliver energy to the fluid in the housing at a level of no less than 10 millijoules per square centimeter.

4. An apparatus according to claim 1 wherein the photocatalyst comprises at least first and second semiconductor photocatalysts.

5. An apparatus for treating fluid comprising:
a housing comprising an inlet for receiving fluid to be treated and an outlet for delivering treated fluid, the housing defining a fluid flow path between the inlet and the outlet;
a light transmitting substrate in the fluid flow path;
a semiconductor photocatalyst adhered to the substrate, the photocatalyst comprising at least a first photocatalyst with a first band gap wavelength;
at least one first light source operable to deliver light to fluid in the housing to be treated said at least one first light source emitting at least one first band of light having a center wavelenghth in the range from 250 nanometers to 285 nanometers so as to provide disinfection treatment of the fluid;
at least one second light source operable to deliver light to the photocatalyst in the fluid in the housing to be treated, said at least one second light source emitting at least one second band of light having a center wavelenghth at or below the first band gap wavelength so as to provide a photocatalytic reduction of contaminant concentrations in the fluid; and
wherein the housing comprises a plurality of chambers, each chamber containing light transmitting substrate with photocatalyst adhered to the substrate, the housing defining a fluid flow path from the inlet through the chambers to the outlet, the apparatus comprising at least three concentric annular chambers comprising right cylindrical chamber walls, the exterior most chamber wall comprising a light reflective material, the other cylindrical walls comprising light transmissive material, an interior lamp receiving chamber being provided within the interior of the innermost annular chamber for receiving at least one first light source, said at least one first light source comprising a low pressure mercury lamp, the at least one second light source comprising a plurality of LED light sources mounted to the walls of the annular chambers.

6. An apparatus according to claim 5 wherein the LED light sources are positioned in light transmitting tubes mounted within at least one chamber.

7. An apparatus according to claim 6 wherein the tubes comprise flexible material which is spirally disposed within at least one of the chambers.

8. An apparatus according to claim 7 wherein the tubes are of a light transmitting fluorinated ethylene propylene (FEP).

9. An apparatus according to claim 8 wherein the light transmissive material is selected from the group consisting of glass, silica, quartz and fluorinated ethylene propylene.

10. An apparatus for treating fluid comprising:
a housing comprising an inlet for receiving fluid to be treated and an outlet for delivering treated fluid, the housing defining a fluid flow path between the inlet and the outlet;
a light transmitting substrate in the fluid flow path;
a semiconductor photocatalyst adhered to the substrate, the photocatalyst comprising at least a first photocatalyst with a first band gap wavelength;
at least one first light source operable to deliver light to fluid in the housing to be treated said at least one first light source emitting at least one first band of light having a center wavelength in the range from 250 nanometers to 285 nanometers so as to provide disinfection treatment of the fluid;
at least one second light source operable to deliver light to the photocatalyst in the fluid in the housing to be treated, said at least one second light source emitting at least one second band of light having a center wavelength at or below the first band gap wavelength so as to provide a photocatalytic reduction of contaminant concentration in the fluid; and
comprising at least one elongated optical wave guide extending into the interior of the housing from a first location, at least one of the first and second light sources being optically coupled to the at least one elongated wave guide with the wave guide guiding light from the said at least one optically coupled light source into fluid in the housing.

11. An apparatus according to claim 10 wherein said at least one wave guide comprises a wall surface and wall surface modifications that diffuse light passing along the wave guide outwardly from the wave guide through the wall surface.

12. An apparatus according to claim 11 wherein said surface modifications comprise one or more of a surface coating, chemical etchings, mold-texturing, photo-ablation, and sand blasted regions.

* * * * *

UNITED STATES PATENT AND TRADEMARK OFFICE
CERTIFICATE OF CORRECTION

PATENT NO. : 9,017,613 B2  
APPLICATION NO. : 13/963602  
DATED : April 28, 2015  
INVENTOR(S) : Owens et al.

Page 1 of 1

It is certified that error appears in the above-identified patent and that said Letters Patent is hereby corrected as shown below:

In the Claims:

Claim 5: Column 17, line 31, "treated said" should read -- treated, said --

Claim 5: Column 17, line 33, "treated said" should read -- treated, said --

Claim 5: Column 17, line 39, "wavelenghth" should read -- wavelength --

Claim 10: Column 18, line 26, "wavelenghth" should read -- wavelength --

Signed and Sealed this  
Third Day of May, 2016

Michelle K. Lee  
*Director of the United States Patent and Trademark Office*